United States Patent
Prieto Barranco et al.

(10) Patent No.: US 8,460,606 B2
(45) Date of Patent: Jun. 11, 2013

(54) AUTOMATIC REACTOR FOR CATALYTIC MICROACTIVITY STUDIES

(75) Inventors: Jose Prieto Barranco, Madrid (ES); Consuelo Goberna Selma, Madrid (ES)

(73) Assignee: Consejo Superior de Investigaciones Cientificas, Madrid (ES)

( * ) Notice: Subject to any disclaimer, the term of this patent is extended or adjusted under 35 U.S.C. 154(b) by 987 days.

(21) Appl. No.: 11/628,335

(22) PCT Filed: Jun. 2, 2005

(86) PCT No.: PCT/ES2005/070079
§ 371 (c)(1), (2), (4) Date: Jul. 10, 2007

(87) PCT Pub. No.: WO2006/008328
PCT Pub. Date: Jan. 26, 2006

(65) Prior Publication Data
US 2008/0063565 A1 Mar. 13, 2008

(30) Foreign Application Priority Data
Jun. 3, 2004 (ES) .................................. 200401347

(51) Int. Cl.
*G01N 33/00* (2006.01)
*G01N 31/00* (2006.01)
*G01N 31/10* (2006.01)
*B01J 10/00* (2006.01)
G01N 31/12 (2006.01)
G01N 7/00 (2006.01)
G01N 30/02 (2006.01)
B01J 19/00 (2006.01)

(52) U.S. Cl.
USPC ................ 422/68.1; 422/80; 422/81; 422/83; 422/129; 422/130; 436/36; 436/161

(58) Field of Classification Search
USPC .................................................. 422/83, 130
See application file for complete search history.

(56) References Cited

U.S. PATENT DOCUMENTS
4,099,923 A * 7/1978 Milberger ...................... 422/80
(Continued)

FOREIGN PATENT DOCUMENTS
DE 24 25 227 3/1975
WO 90/12317 10/1990

OTHER PUBLICATIONS

"Standard Method for Testing Fluid Cracking Catalysts by Microactivity Test," Designation: ASTM D 3907-87, 1987, pp. 825-829.

P.M. Michalakos et al., "Catalyst deactivation in the cracking of hexadecane and commercial FCC feed as studied by microactivity test-multiple cold trap (MAT-MCT) technique," Catalysis Today 46 (1998), pp. 13-26.

(Continued)

*Primary Examiner* — Bobby Ramdhanie
*Assistant Examiner* — Jennifer Wecker
(74) *Attorney, Agent, or Firm* — Wenderoth, Lind & Ponack, L.L.P,

(57) ABSTRACT

The invention relates to a reaction device which is used to study the behavior of a catalyst in the presence of reactants. The inventive device includes: various different mass flow regulators, which are used to supply a known controlled stream of gases, a pump which supplies the system with liquid reactants from a container, a hot box, wherein there have been placed a supply current evaporator and preheater, a valve which can be used to select the process path, a reactor into which the catalyst is introduced inside a furnace, a system which can be used to separate the liquid and gaseous products by cold condensation under pressure and which controls the pressure in the line of output gases, and a system for controlling the level in the decantation operation, the system being automated and computerized.

6 Claims, 6 Drawing Sheets

U.S. PATENT DOCUMENTS

| | | | |
|---|---|---|---|
| 5,266,270 A * | 11/1993 | Ajot et al. | 422/80 |
| 6,086,832 A | 7/2000 | Ohta | |
| 6,497,844 B1 * | 12/2002 | Bacaud et al. | 422/68.1 |
| 6,673,741 B2 * | 1/2004 | Kang et al. | 502/323 |
| 7,285,261 B2 * | 10/2007 | Mukhopadhyay | 423/592.1 |
| 7,419,830 B2 * | 9/2008 | Canos et al. | 436/37 |
| 2004/0149032 A1 * | 8/2004 | Sell | 73/304 C |
| 2005/0003552 A1 * | 1/2005 | Canos et al. | 436/37 |
| 2005/0016828 A1 * | 1/2005 | Bednarek et al. | 203/1 |

OTHER PUBLICATIONS

"Standard Test Method for Testing Fluid Catalytic Cracking (FCC) Catalysts by Microactivity Test", Designation: ASTM D 3907-03, May 11, 2006, pp. 1-6.

* cited by examiner

AUTOMATIC REACTOR FOR CATALYTIC MICROACTIVITY STUDIES

BACKGROUND OF THE INVENTION

I. Field of the Invention

This invention relates to an automatic reactor for catalytic microactivity studies, based on a hot box system, which is especially conceived for studying the behaviour of a catalyst in the presence of some reactants and how this alters the activity and selectivity of a defined chemical reaction.

The automatic reactor proposed by the invention is in the field of two different sectors, industry and research. At the industrial scale this type of equipment will be able to be used primarily in the search for suitable catalysts for a process and obtaining of the optimum operating parameters. At the research level, it will primarily be used for evaluating activity and selectivity in the development of new catalysts.

The object of the invention is therefore to provide a reactor which achieves certain levels of repeatability, reliability of results and automation much higher than those obtained by commercial systems currently in existence.

II. Description of the Related Art

In the field of heterogeneous catalysis it is very complicated to predict the catalytic behaviour of a material solely on the basis of its composition and/or chemical structure. For that reason, the only way to determine whether such a material possesses good catalytic properties for a chemical reaction is to conduct an activity test under the same operating conditions as the process of interest, which usually lie in the following intervals:

Pressure: 10-90 bar
Temperature: ambient—750° C.
Charge: Liquid and/or gases: Stream of reactants: 0.01-100 VPH (volume of charge per unit of catalyst and per hour) for liquids and 10-100,000 for gases.
Solid catalyst (balls, pellets, extruded particles, etc.).

When the aim is to measure the catalytic activity of a solid under conditions close to or identical with those used in the industrial process, the pilot plants that are currently available display a series of difficulties, especially in situations in which one is working at pressure above atmospheric:

Large quantities of catalyst are required, which implies a serious obstacle when its preparation is complicated or very costly.
The activation and stabilisation of the system under the desired operating conditions take long periods of time (hours, or even days), due to the thermal inertia of the equipment and dead spaces.
The majority of the usual facilities do not permit automatic on-line analysis with the reactor which would entail continuous analysis and short response times.
The complete automation of the system of a standard facility and its control by computer is a very complex and a highly expensive operation.
The achievements in accuracy and reliability in this type of equipment are limited, due both to reasons that are intrinsic to the system (lack of stability of the catalyst in very large time periods) and also extrinsic (difficulty when it comes to having a system free of fluctuations when modifying the reaction parameters).

This need to conduct activity tests under conditions identical to those used in industrial reactors has led to the development of microactivity reactors, with associated systems of sampling and analysis of the reaction products which make it possible to obtain a rapid response from the system in each catalytic evaluation. This objective is achieved by means of a reduction in the reaction times, associated with the small quantities of catalyst required and the small dimensions of the reaction equipment.

In the majority of equipments with which one works at atmospheric pressure, the liquid/gas separation is done by passing the reaction products through a refrigerated tank, like that described in regulation ASTM D3907-80 for the MAT of FCC catalysts, and sometimes exerting a slightly negative pressure of −60 mbar, subsequently quantifying the reaction liquids by weighing and quantifying the gases in a totaliser by displacement of water. In patent ES9000012, J. Prieto, A. Corma and F. Melo describe an automated MAT reactor for carrying out consecutive sequences of reactions without the presence of an operator.

But in microactivity equipment working at pressures above atmospheric, it is necessary to determine the compositions of the output effluents from the reactor at the reaction temperature and pressure. The separation of phases is currently carried out inside a liquid-gas condenser/separator capable of performing this operation at high pressure, thereby increasing the efficiency of the system. With the aim of avoiding the accumulation of liquids inside the separator, a reading of the level of liquids permits control over it, with continual evacuation of as much liquid as is condensing in the system in real time. This operation is currently carried out in commercial equipment by measurement of the differential pressure in the condenser, permitting indirect measurement of the level. But, owing to the dead volume associated with the measurement in the separator, the limitations associated with this technique are very considerable, since in a catalytic microactivity reaction, where the streams of liquid are of the order of 0.05 ml/min, the first drop of sample product of the reaction would be evacuated from the system hours after the start of the reaction. So, with this system it is impossible in real time to have samples of the reaction products at very short reaction times (of great interest for studies of reaction kinetics) and without contamination as a consequence of dilution inside this separator.

At the outlet from the condenser, and once the phases have been separated, a valve, associated with a pressure sensor, acts on the gas stream evacuating from the reactor, keeping the pressure of the system constant. But this operation, carried out with the pressure control devices commercially available right now, is done at the cost of generating some characteristically pulsating gas streams in the reaction system, which has an appreciable effect on the reproducibility and reliability of the results obtained. Certain electronic elements for pressure control upstream available on the market manage to get around these effects, but their use is not possible when there exist condensable vapours in the system.

Once the separation has been carried out, the reaction gases are analysed by gas chromatography, either in a subsequent stage or by means of on-line analysis. One of the limitations of this type of analytical system is the long analysis times that are required, which makes it impossible to have analysis at short reaction times. As a possible solution to this problem, H. Ajot (U.S. Pat. No. 5,266,270 A) developed a catalytic microactivity unit with a system of sampling valves, provided in the furnace, in series and parallel, at the outlet from the reactor, which would permit the gathering and storing of outlet effluents in different compartments of known volume at high temperatures (from 50 to 300° C.), avoiding the condensation of heavy products. This system allows reaction samples to be taken at reaction times as short as is wished in order later on to analyse them successively by gas chromatography.

P. M. Michalakos et al (Catalysis Today 1988, 46, 13-26) applied a similar system of sample taking to a microactivity reactor for fluidised bed catalytic cracking reactions based on standard ASTM D3907, to which he coupled a system of ten cold traps (MCT system, Multiple Cold-Trap, Chevron patent) in which the products were condensed and stored at the desired reaction times for their later evaporation and analysis by gas chromatography. In both cases, the reaction sample is taken without separation of liquids and gases, and is advantageous when it comes to testing catalysts which are rapidly deactivated at small reaction times. But in neither of these two sampling systems that have been developed is it possible to carry out a strict material balance, since there is no on-line analysis available of the effluents in the reaction conditions under pressure. Moreover, the monitoring of the catalytic reaction continues to be limited and conditioned by the long analysis times that are required in this type of system. So, it is impossible to act on the reaction parameters as a function of the analyses obtained in real time.

On the other hand, E. C. Milberger, in U.S. Pat. No. 4,099,923, describes an automatic unit for the preselection of catalysts, obtaining a preliminary indication of its potential activity. H. Kögler in DE 2 425 227 describes an automatic microreactor for studying catalytic reactions under pressure. But none of these documents suggests carrying out a complete material balance of the chemical reaction under pressure, determining the outlet stream from the reactor at its pressure and temperature, a measurement which cannot be made in any direct way.

There are few highly automated microactivity equipments described in the literature. On the contrary, most of them have a very low level of automation, requiring close attention and dedication by the operator. Works published in 1998 can be highlighted, in which the incorporation of a computer that would control the process was predicted for the future, and mention can also be made to U.S. Pat. No. 5,266,270 which incorporated programmable controllers into a MAT type reactor, the automation of which permitted good reproducibility and reliability in the results obtained.

In the catalytic microactivity reactor described in U.S. Pat. No. 6,497,844, the control of the streams of reactants is done by means of valves, and the control of pressure and temperature in the system is done by means of PID controllers, with the reference point being able to be transmitted by an RS-485 type connection. The system is provided with safety measures in the event of a failure in the system, so that if a regulating element (thermocouple, valve, pressure sensor, etc.) fails, the controllers cancel the specified reference point and the system stops in a "safety" status. The elements of the system are connected to a computer in such a way that the software used guarantees operation in sequential mode, along with recording of the different parameters of the process. But this system, controlled solely by means of computer, does not provide for control of the system in the event of a failure in the computing system, which would leave the system out of control.

So, as has been confirmed, current systems display drawbacks such as the high cost of this type of equipment on the market, even when their performances are low and their level of automation is relatively poor.

SUMMARY OF THE INVENTION

The automatic reactor for catalytic microactivity studies which the invention proposes resolves in a manner that is entirely satisfactory the problems stated above, in the different aspects commented upon.

The catalytic microactivity reactor includes a system formed from several mass flow controllers, which supply a known controlled stream of gases, a feed pump for liquid reactants, a hot box and/or evaporator for the supply stream, a valve or bypass for the reactor which permits to select the process path between the reactor and analysis without passing through the reactor, a reactor for working at temperatures of up to 800° C., or higher by using special materials, and the separation system for liquid and gaseous products by means of cold condensation under pressure which incorporates the pressure control in the output gas line, and a system for controlling the level in the decantation operation.

The gas streams pass through a shut-off valve and are fed into the system by means of mass flow controllers (MFCs), which measure and control the mass flow of each gas. In order to prevent undesired products from returning via the line towards the MFCs, the latter are protected with non-return valves, made of an elastomeric material chemically compatible with most of the compounds that might be present or be formed in the system.

The stream of liquids is dosed by a pump, with a pressure regulator upstream that considerably improves its functioning. The liquids are introduced into the system via a non-return valve with low dead volume.

The liquid and gas streams are introduced into a hot box system which permits the process to be traced at temperatures between 160° C. and 190° C., with the aim of avoiding possible condensations in the lines of the system, valves, joints, etc. In order to keep the temperature in this hot box controlled, a heating system is used. It is obvious that the highest temperatures in this system will be found in the vicinity of the outlet of the stream from this heater and so a preheater-evaporator for the liquids has been located at temperatures 15-20° C. above the rest of the system. Also, the system includes a preheater for the gases, at temperatures 10-15° C. above the rest of the system.

Once the liquids have been preheated and the gases have been evaporated, these streams are combined together and sent to a valve, preferably six-way, though it could be four-way or any other valve which, by means of remote pneumatic action, permits the path of the stream to be selected between two possible alternatives: diverting it towards the reactor or selecting a path which prevents this. This valve permits the stream of reactants to be diverted towards the analysis technique without previously passing through the reactor.

In the case of diverting the stream of reactants towards the reactor, the stream passes on the way through some filters, both at the inlet and at the outlet of the reactor, which protect the system from possible contaminants, such as might be finely divided particles of catalyst.

The reactor used must have connections that can withstand high pressures, which show good performance towards cooling and heating at high temperatures without any deterioration or leaks in the system.

The system incorporates a thermocouple in the bed of the catalyst, without the use of a thermowell. This allows readings to be taken of the reaction temperature with response times of milliseconds and, therefore instantaneously control action towards changes in the reaction temperature. The furnace in which the reactor is found includes a refractory material containing a resistor, suspended inside a casing, without insulation, in such a way that it dissipates heat rapidly and without inertia. Also, its dimensions will be such that permit the reactor to be entirely encased in order to improve the heat transfer.

At the outlet from the reactor, and after passing through the valve, the reaction products are sent to the outside of the hot box, where a liquid-gas separator of low dead volume and with a high resolution level sensor is installed, permitting condensation of the liquids and their evacuation from the system when the accumulated volume is from 0.1 to 0.5 cm$^3$, even in systems at a pressure of 60-120 bar. The continuous functioning of this system enables samples of liquids to be obtained at extremely short times and without accumulation or dilution with time. A servo-positioned micrometer control valve, actuated by a signal from the level controller which receives the signal from the capacitive type sensor installed in the system, allows one to work with extraordinary precision.

The separator has an outlet for gases which circulate towards the pressure control system, including a servo-positioned micrometer control valve with a very high useful scale of work, and which is at high temperature. The precision in the pressure control is high and the gas stream at the outlet is continuous and constant.

A very important feature of the system which the invention proposes is the absence of dead volumes, which means that all its components will be selected bearing this characteristic in mind, and in some cases special parts need to be designed that will eliminate undesired dead volumes in the system.

With the aim of avoiding the large number of joints necessary for the supply system for various gases and with the aim of favouring their mixing, a piece has been incorporated into the system which reduces the number of joints and which contains inside it a coil element which forces the circulation of the gases through the wires of this coil, thus favouring their mixing.

The proposed system is automated and computerised, it has local control and remote control on-line, based on digital communications with distributed control structure. This distributed control structure communicates with the outside by means of a TCP/IP protocol via Ethernet. The safety system for the equipment is integrated into a microprocessor independent of the computer. In this way, the alarm signals from the different control loops are centralised in the microprocessor which acts according to its programming with regard to the different alarm situations of the system. These actions occur autonomously and instantaneously, independently of communications with the computer, which results in increased safety of the system, which not only continues with its activity in the event of a failure in the computing system but also its safety system remains operational.

The reactor proposed by the invention uses closed control loops with feedback of the signal of the proportional, integral and derived type. The different parameters to control, along with the information provided by the system, can be displayed on a monitor connected to the computer.

According to what has been stated above, the control of the reaction temperature is carried out with the thermocouple located in the bed of the catalyst, and the signal emitted by it is evaluated by the controller, in such a way that its output signal is sent to a system which regulates the power supplied to the furnace in a way that is proportional rather than being on-off. The alarm from this controller actuates its output signal, the heater for the hot box, the gas supply and the liquids pump.

The temperature of the hot box is controlled in the same way, though in this case the signal is emitted by a thermocouple located inside that box. The alarm for this controller acts on the turbine for the heater, preventing it from stopping while the heater is at high temperature.

In terms of pressure control, the signal from the pressure transmitter installed downstream of the reactor is evaluated by the controller in such a way that its output signal determines the position of the pressure control valve, which is of the micrometer regulation type and servo-controlled. Its alarm acts on the mass flow controllers and the liquids pump, and is of the self-locking kind in order to prevent a repetitive cycle of the system in the event that its activity ceases even when the problem that caused it has not been solved. Once the pressure alarm is activated, the system will remain on stand-by until the operator acts manually in order to disable this locking, an action that will be performed once a check has been made of the system and the anomalous situation has been prevented.

For the level control, the signal from the level sensor, which is capacitive type for microvolumes, installed in the liquid-gas separator, is evaluated by the controller, in such a way that its output signal determines the position of the level control micrometer valve with serve-controlled regulation located in the base of the separator. Its alarm acts to halt the supply of liquid to the reactor.

The control system for the reactor sends the control signals to the mass flow controllers. The system recognises the output signal from the flow controllers and compares them with the reference, generating an alarm system in the event that they do not coincide.

The alarms of the system will be managed by means of a programmable automaton, microprocessor or microcontroller. The alarm signals permit a situation of safety to be created in the event of, for example, a failure in the power supply feeding the system or a return of stream in the control valves, and there are also alarms for the temperature controller, for the functioning of the hot box, for the detector that the hot box door is closed, the detector for furnace closed, for stream, pressure, level and an outside or general alarm for the system.

The automatic reactor for catalytic microactivity presents a series of advantages or improvements compared to other existing systems, said improvements being due to the incorporation into the system of elements such as the liquid-gas separator with low dead volume with continuous level measurement, permitting liquid samples to be obtained at a reaction time of minutes, the use of the hot box and a pressure control system of the motorised servo-valve type which permits precise control of the pressure with high stability in the stream of gases in the system, and which admits thermostatisation at temperatures of up to 200° C.

DESCRIPTION OF THE DRAWINGS

In order to complement the description that is going to be made, and with the aim of aiding a better understanding of the characteristics of the invention, in accordance with a preferred example of practical embodiment thereof, this description is accompanied by a set of drawings containing figures which, on an illustrative rather than limiting basis, the following have been represented.

DETAILED DESCRIPTION OF THE INVENTION

Figure 1:
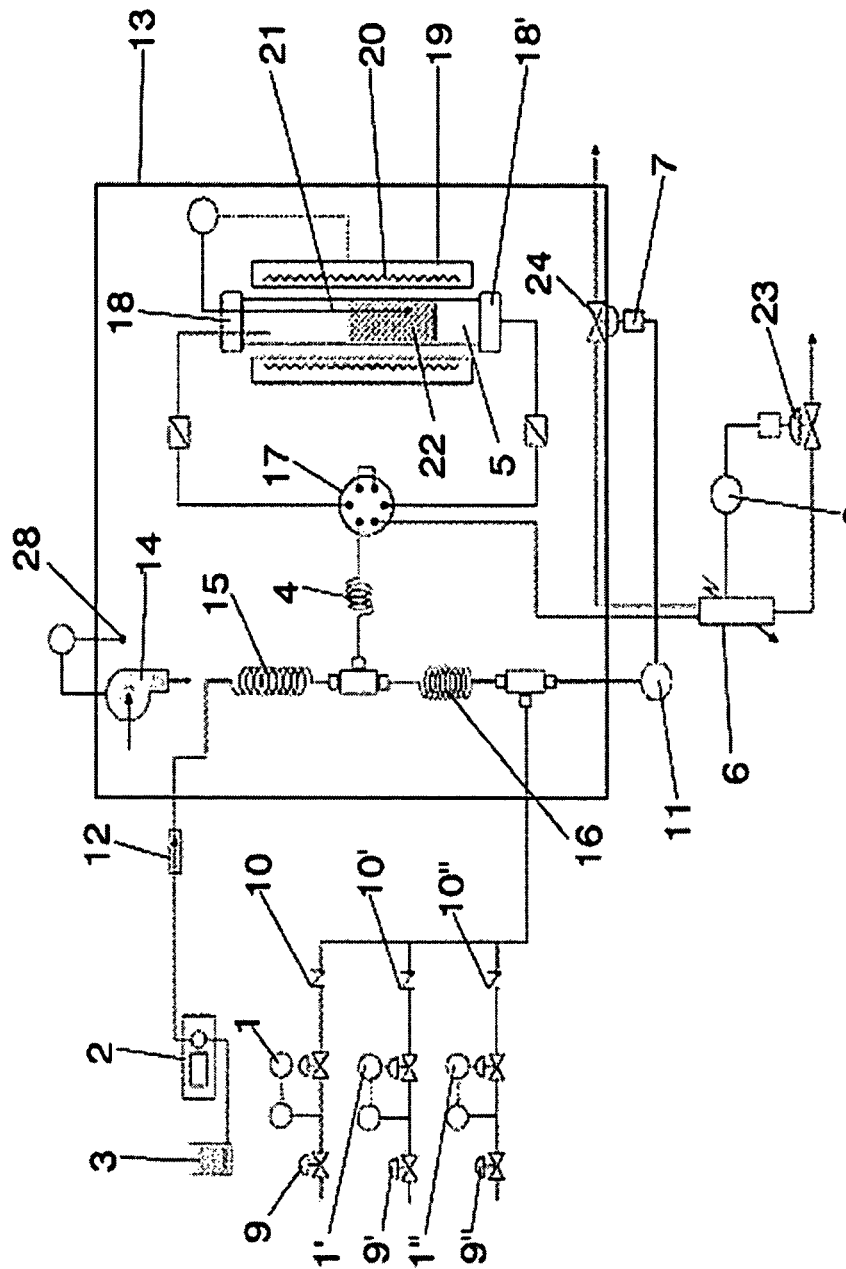
FIG. 1 shows a schematic diagram in which the different components are represented constituting the automatic reactor for catalytic microactivity studies forming the object of the invention.

With the commented figures in view, specifically FIG. 1, it can be seen how the automatic reactor for catalytic microactivity studies which the invention proposes essentially includes a system formed from various different mass flow regulators (1, 1', 1"), in the example there are three though there can be more, which are used to supply a known controlled stream of gases, a pump (2) which supplies the system with liquid reactants from a container (3), a preheater and/or evaporator (4) for the feed stream, a reactor (5) and separation system (6) for liquid and gaseous products by means of cold condensation under pressure and which incorporates the pressure control (7) in the gas output line, and a system (8) for controlling the level in the decantation operation.

The system is thus fed by a stream of gases and by another stream of liquids. The gas streams pass through a cut-off valve (9, 9', 9") and are introduced into the system by means of mass flow controllers (1, 1', 1"). In order to prevent unwanted products from returning through the line to those controllers, some non-return valves (10, 10', 10") are then located, with a kalretz elastomer. The stream of liquids, for their part, is usually provided by an HLPC pump (2), with alternative positive displacement; this is a pump that works with flows of between 0.005 and 5 ml/min and pressures of up to 600 bar, with a pressure regulator (11) downstream of 30 bar at its outlet which improves its functioning. The liquids are introduced into the system via a non-return valve (12) of low dead volume, and with a rupture pressure of 10 psig.

In order to avoid a large number of joints necessary for the supply system for various gases and with the aim of favouring their mixing, the system incorporates a stainless steel distributor, which reduces the number of joints and which contains inside it a coil element which forces the circulation of the gases through the wires of this coil, thus favouring their mixing.

The liquid and gaseous streams are introduced into a hot box system (13) which is kept at a temperature of 160° C., and exceptionally even at 190° C., preferably made of stainless steel, and which includes a hot air convector.

In order to join the liquid non-return valve (12) and the hot box (13), a long male hose is used. Its purpose is, on account of its relatively large mass since it includes a solid piece, to transmit the temperature of the hot box (13) to the non-return valve (12). It has a high dead volume, for which reason it incorporates a series of Teflon parts which reduce the cross-section of the throat, along with other pieces which reduce the dead volumes of the joints.

In order to keep the temperature of the hot box (13) controlled, an electric heater (14) is used, which functions by forced convection, and a turbine. For its proper functioning, at the same time as the heater (14) is functioning, the turbine has to do so as well, in order to dissipate the heat and prevent deterioration of the heater. In the vicinity of the stream outlet from this heater (14) the highest temperatures are to be found and for that reason, just at that point, beneath the forced stream from the heater (14) there is a preheater-evaporator (15) for the liquids which is at a temperature of 20-25° C. above the rest of the system, in other words at around 200° C., and a preheater (16) for the gases at a temperature of 10-15° C. also above the rest of the system, in other words at around 190° C.

Once these inlet streams have been preheated, and the liquids have been evaporated, they are joined in order to be sent to a valve (17) which, in a preferred embodiment of the invention, is six-way though it could perfectly well be four-way, however six-way allows, for example, pre-treatments to be carried out at atmospheric pressure while the feed stream is being evaluated by chromatographic techniques. This valve (17) can work at 200° C. and 100 bar and it permits the inlet stream to be diverted towards the reactor (5) or towards the analysis technique without previously passing through the reactor (5).

Both at the inlet and at the outlet of the reactor, the streams of reactants meet up with some filters (18, 18'), preferably made of stainless steel, with a porous plate of 10 m and intended to protect the system from possible contaminants such as might be finely divided particles of catalyst.

The reactor (5) is preferably manufactured in stainless steel, and in the example of this embodiment it is a tubular reactor, whose dimensions or measurements will depend on the specific needs of each system. It is installed inside a furnace (19), which has no insulation that would damp its response speed, thereby optimising the design and response of the system. The furnace (19) includes a refractory material containing a resistor (20) suspended inside a stainless steel casing without insulation, in order thereby to dissipate the heat quickly and without inertia. The shape and measurements of the furnace (19) are such that they permit the entire surface of the reactor (5) to be encased, thus improving the heat transfer. The furnace (19) is hinged and has an automatic opening mechanism.

Introduced via the upper part of the reactor (5) is a thermocouple (21), encapsulated in a sheath, which is in contact with the bed (22) of the catalyst providing measurements of reaction temperature with response times of milliseconds.

The reaction products exit from the reactor (5) in order to pass again through the six-way valve (17), and are then sent to the outside of the hot box (13), where a liquid-gas separator (6) of low dead volume is installed, permitting condensation of the liquids and their subsequent evacuation from the system when the accumulated volume in the tank of the separator (6) reaches from 0.8 to 0.3 $cm^3$, in systems operating at a pressure of 90 bar. By means of a servo-positioned micrometer control valve (23), actuated by a signal from the level controller (8) which receives the signal from a capacitive sensor installed in the system, the operation of evacuating the liquids as they condense in the separator (6) is carried out with extraordinary precision, of ±0.1 $cm^3$.

In the upper part of said separator (6) is the outlet for the gases, which are sent to the pressure control system (7), consisting of another servo-positioned micrometer control valve (24) which is located inside the hot box (13) and is therefore at high temperature. The valve (24) permits a continuous and constant gas stream to be obtained at the outlet.

The reactor is complemented with the corresponding automation and computerisation systems. It has local control and remote control on-line, based on digital communications with distributed control structure which communicates with the outside by means of a TCP/IP protocol via Ethernet. A microprocessor independent of the computer permits the safety system to be integrated in such a way that the alarm signals from the different control loops are centralised in the microprocessor which acts with regard to the different alarm situations of the system that have been programmed The automation of the unit permits a situation of safety to be provided in the event of a failure in the power supply. As a first safety measure, the controllers store in their non-volatile memory the latest parameters introduced manually from their keyboard. In the event of a power failure, the plant returns to those safety values or parameters, independently of what the latest values sent by the computer might be.

As a precaution, the safety values of the system have to be reintroduced following any manual modification to the reference point in operations performed by the operator, independent of the computerised control system.

Another safety system includes a temperature controller alarm, of the absolute and upper limit type, which deactivates the control signal of the furnace (19) of the reactor (5) and of the heater (14) for the hot box (13), and it halts the functioning of the flow controllers (1, 1', 1"). It also halts the functioning of the HPLC pump (2), it activates a sound alarm as a warning signal for the operator and it activates the inhibition function of the safety system, preventing the software from changing session.

Figure 2:
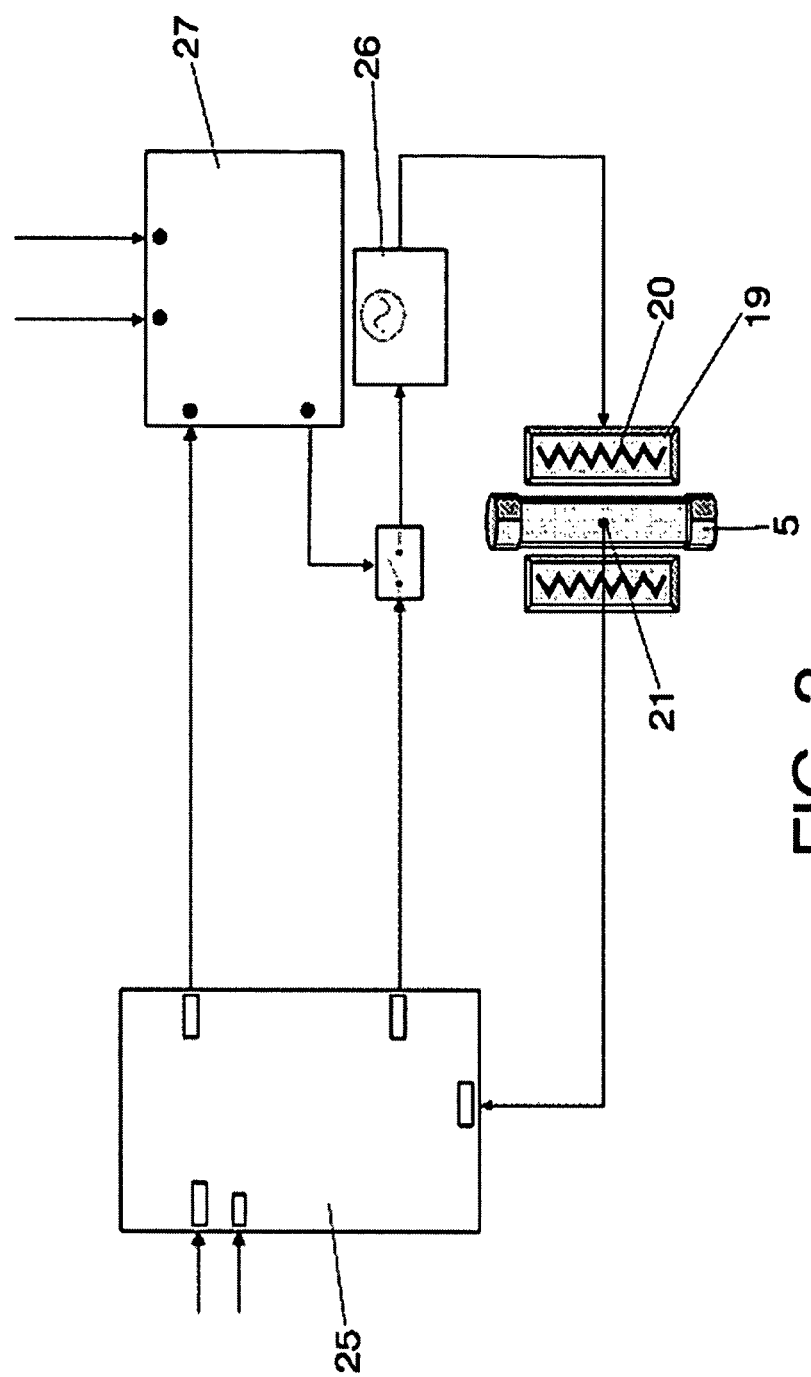
FIG. 2 shows a block diagram in which the control loop for the temperature of the reactor has been represented.

The control loop for the temperature of the reactor according to FIG. 2 includes a controller (25) of that temperature as far as the arrival of a signal coming from the thermocouple (21) located inside the reactor (5), the controller (25) provides an output signal of the type 4-20 mA which is sent to a proportional solid state relay (26) of the zero-pass type, which regulates the power supplied to the furnace (19) on a proportional basis. The system is complemented with a programmable automaton (27) for management of the alarm, at the prototype level, or a microprocessor at the level of series equipment for industry.

Figure 3:
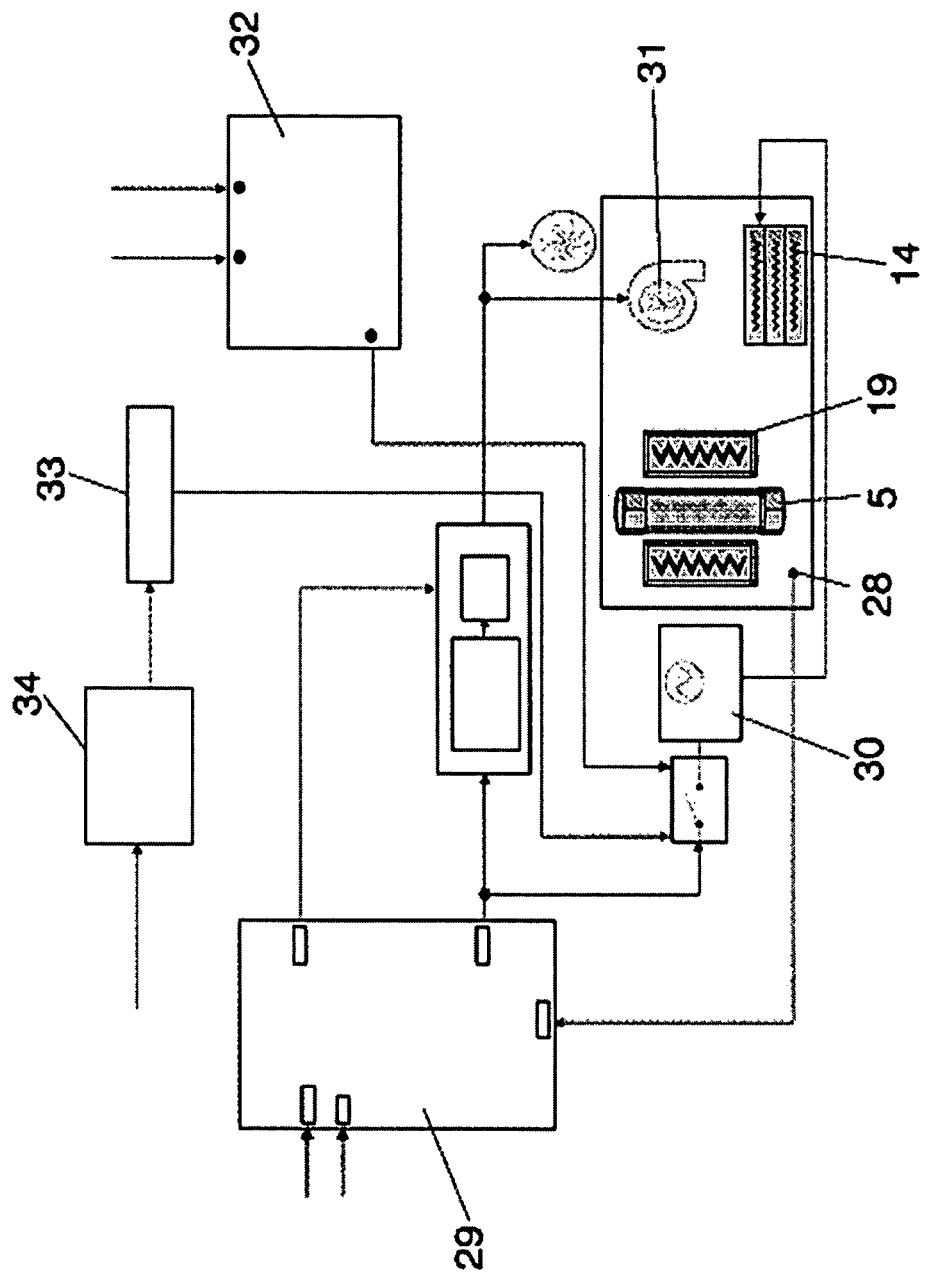
FIG. 3 shows a block diagram in which the control loop for the temperature of the hot box has been represented.

In the case of the hot box (13), whose temperature control loop appears in FIG. 3, the signal from the thermocouple (28) located inside it is evaluated by the controller (29), its output signal of 4-20 mA is sent to a proportional solid state relay (30) of the zero-pass type, which regulates the power supplies to the heater (14) for the hot box (13) on a proportional basis. Moreover, the alarm from this controller (29) acts on the turbine (31) of the heater (14), such that, whenever the controller (29) sends a control signal greater than 5 mA to the proportional solid state relay (30) governing the power of the heater (14), the turbine (31) comes into operation. So, even if this signal does not exist, whenever the temperature of the hot box (13) is greater than 40° C. the turbine (31) will be functioning.

With the aim of cutting off the power supplied to the heater (14) for the hot box (13) when its door is opened, there exists a door-open detector (33) with a power supply source (34), which is an inductive pick-up which recognises the status of that door. This function does not halt the functioning of the turbine (31) nor does it act on the rest of the system.

There also exists a furnace-closed detector, with the aim of cutting off the power to the heater (14), the hot box (13) and the furnace (19) of the reactor (5) when the furnace is open. The detection of furnace open halts the functioning of the heater (14), the hot box (13) and the power supply to the furnace (19) and it prevents the operation of the mass flow controllers (1, 1', 1") for the reactive gases, without affecting the functioning of the gases selected as inert, and it activates the inhibition function for the safety system, preventing the computer program from changing the work routine. If the hot box (13) is automatically opened during a reaction procedure, the reaction furnace (19) will also open and the flow controllers (1, 1', 1") for the "non-inert" gases will close, in addition to the power supply to the furnace (19) being cut off. For that reason, if the door of the hot box (13) needs to be opened, this must be done manually without using the push-button for opening the door. Manual opening of the door will only halt the power supply to the heater (14) for the box (13).

Figure 4:
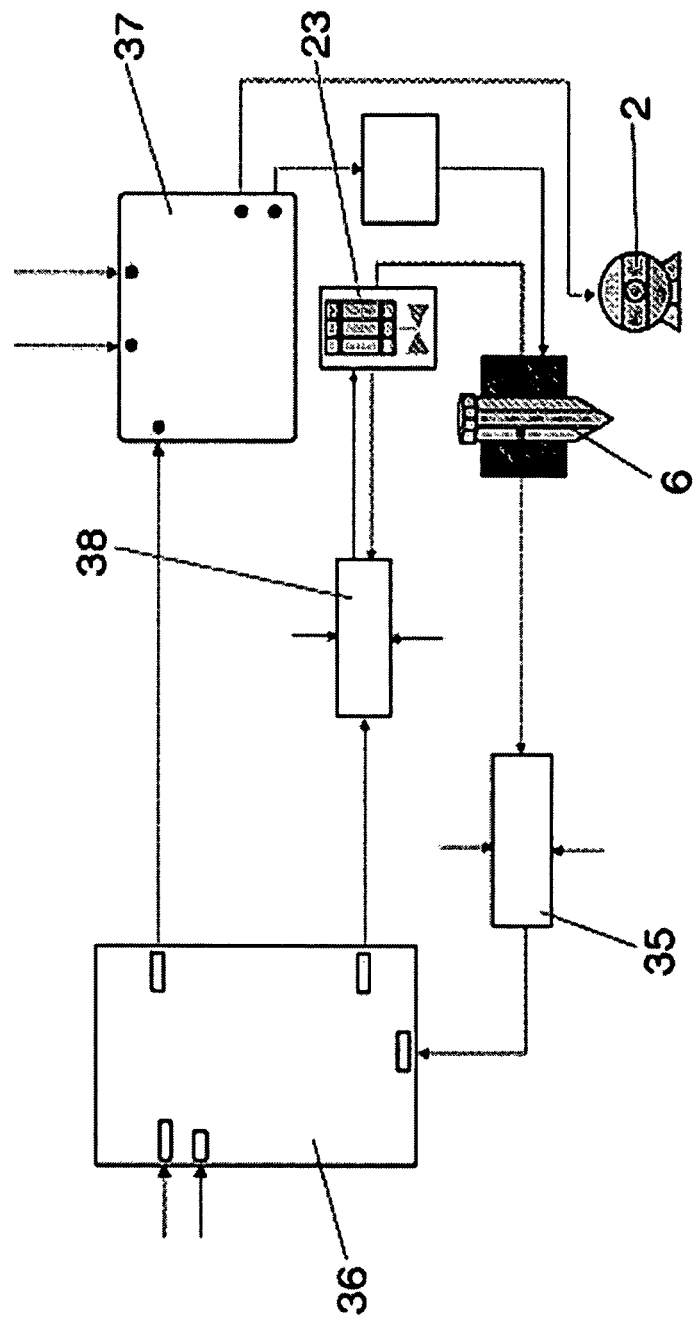
FIG. 4 also shows a block diagram for the control loop for the level.

In terms of level control, represented in FIG. 4, the capacitive sensor (35) for the liquid-gas separator (6) provides a signal which is evaluated by the controller (36) in such a way that the 4-20 mA output signal determines the position of the level control valve (23) by means of an electronic controller (38). The alarm is of the absolute type, it is managed by the automaton (37) or microprocessor, and it generates the detection of the pump (2) for the supply of liquids and activation of the sound signal and of the inhibition function when a prefixed upper limit is exceeded.

Figure 5:
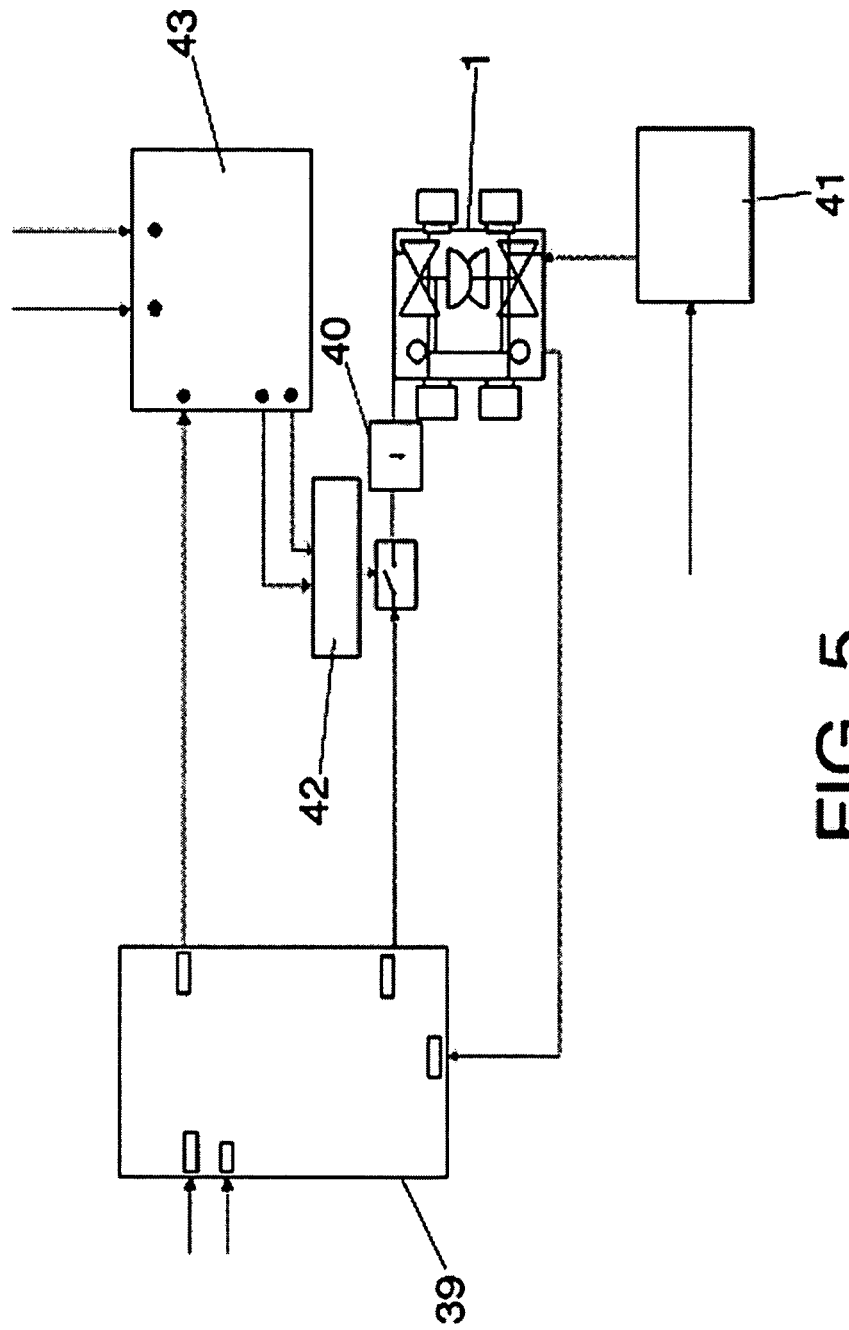
FIG. 5 shows another block diagram for representing the control loop for the flow.
Figure 6:
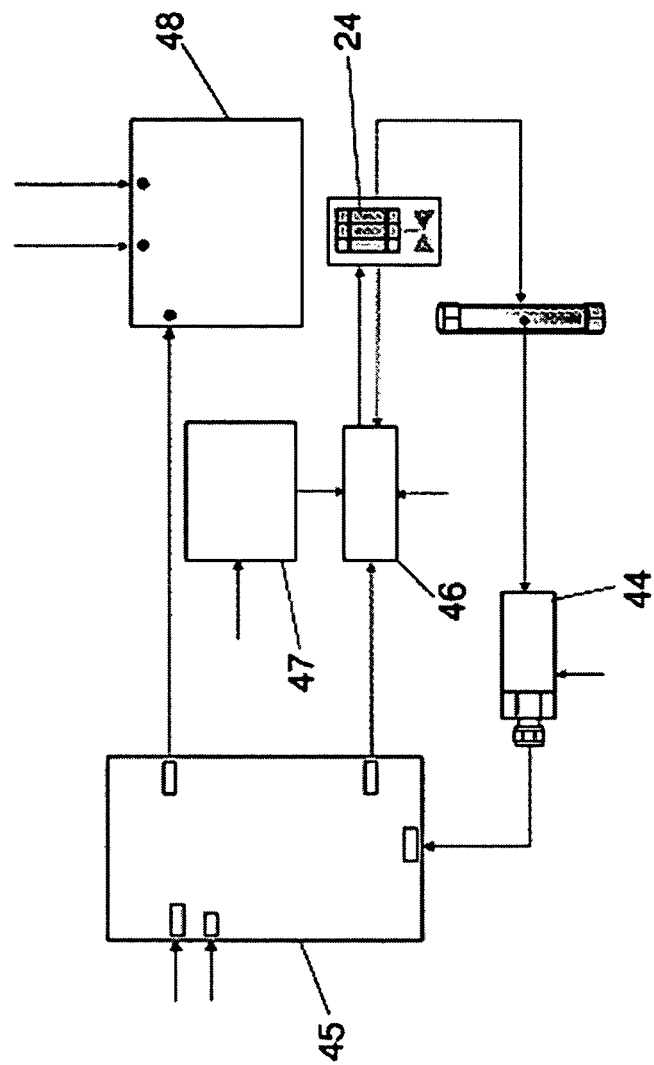
FIG. 6 finally, shows another block diagram in which the control loop for the pressure has been represented.

Another type of alarm incorporated into the system is that of flow control, which appears represented in FIG. 5. The instruments used for the dosing of the gases to the system are in themselves flow controllers. The flow control system (39) is therefore limited to sending the 0-5 VDC control signals to the mass flow controllers (1), which are fed with power from a power supply source (41). This system recognises the 0-5 VDC output signal from the mass flow controllers (1) and it compares it with the reference, generating an alarm signal (42) managed by the automaton (43) or microprocessor, in the event that they do not coincide. This alarm is one of percentage deviation on the reference point. If the reference flow is exceeded for more than 10 s by more than 10% of its value, then the system halts the functioning of the furnace (19) of the reactor (5), a sound alarm signal is generated in order to warn the operator and the inhibition function of the software is activated with the aim of preventing any changes of work session.

There is also a control and alarm system for the pressure. The signal from the pressure transmitter (44) fitted downstream of the reactor is evaluated by the controller (45) in such a way that its 4-20 mA output signal determines the position of the pressure control valve (24). The alarm for the system, managed by the automaton (48) or microprocessor, acts on the mass flow controllers (1, 1', 1") and the liquids pump (2), and is of the diversion type, such that it acts both in the event of the reference pressure being exceeded, and in the event that fails to reach the prefixed margin. The safety system remains like that until an operator acts on the reset for the pressure alarm, once the source of the problem has been located.

The final elements for pressure and level control are servo-positioned microregulation valves. A failure in the control system for these valves generates an alarm of the same nature as that generated by their master control loops. A failure in the pressure control valve (24) generates a similar action to that generated by a pressure alarm, and a failure in the level control valve (23) generates an action similar to that occasioned by an alarm from the level controller (8) in the separator (6).

A signal coming from an external gas detection system or similar can trigger a general alarm in the system implying the halting of the heater (14) for the hot box (13), the reaction furnace (19), all the mass flow controllers (1, 1', 1"), the liquids pump (2), activation of the sound alarm and generation of the inhibition signal for the system.

In order to carry out a reaction in the microactivity reactor (5), and once the reactor (5) has been charged with the catalyst it is wished to test, one proceeds to programme the sessions of the process in the control program for the plant (computerised system with distributed control). These sessions will specify the operating conditions with which the reaction is going to be carried out. The parameters which will have to be specified in each of the sessions are:

Operating conditions of the system: temperature of the reactor (5), temperature of the hot box (13), pressure of the system, stream of reactants (gases and/or liquids).
The controller for each of the variables of the system is represented by a device by means of which the reference point of the variable can be modified, along with its main control parameters (P, I, D, SLL, SLH, etc.).
Status of the six-way valve (17): in reaction or in bypass.
Status of the liquids tank; refrigerated or not.
Length of time of the session.
Session with which it has to be linked.

All the sessions will be linked together. The order in which the sessions have to be executed is in general:

A first session is programmed with the operating parameters corresponding to a safe shutdown of the system: temperatures at 0° C., atmospheric pressure, absence of streams of reactive gases, cooler off and six-way valve (17) in bypass mode.

A second session takes the system to the operating conditions starting from which it is wished to commence the reaction (e.g.: heat the reactor (5) to the working temperature). This session must last for the length of time necessary so that the system has enough time to reach the required operating conditions, and is usually done in the presence of a small stream of inert gases circulating through the reactor, with the six-way valve (17) in the "reaction" position.

Subsequent sessions correspond to the operating conditions in which the reaction is carried out. The length of time for each session will have to be that necessary so that the system has enough time to become stabilised from one session to the next.

The last two sessions correspond to safe shutdown of the system.

The communication between the computer and the control system is based, for example, on RS-485 digital communications. The interface with the operator is, for example TCP/IP via Ethernet.

An example of a sequence of sessions is that used for the reaction involving the oxydehydrogenation of ethane with $CO_2$, in which four different streams of reactants are established for three different reaction temperatures: 700, 720 and 750° C. The system is maintained at each of the operating conditions for 30 minutes, except in those sessions in which a stepwise increase in temperature is programmed, in which it is maintained for 45 minutes. This time is more than enough for stabilising the system and obtaining representative and reliable data on the reaction, which implies a major saving in time compared to the mode of operation in a conventional microactivity reactor. So, in one series, it is possible to perform 12 different experiments in order to evaluate a single catalyst under different operating conditions in just 9 hours, including the time needed for start-up and safe shutdown of the equipment.

During the entire length of time that the experiment lasts, the system operates in a fully automatic mode, without the need for any intervention by the operator. The sessions are linked with each other in consecutive mode.

The invention claimed is:

1. An automatic reactor system for catalytic microactivity studies, said automatic reactor system comprising:
    a hotbox;
    a furnace disposed inside said hotbox;
    a reactor positioned inside said furnace disposed inside said hotbox and having a catalyst disposed therein;
    a plurality of mass flow controllers, said plurality of mass flow controllers configured to supply a known controlled stream of gases to said reactor;
    an HPLC pump configured to supply liquid reactants from a container,
    said hot box comprising a preheater for the gases and a preheater-evaporator for the liquid reactants;
    a valve disposed inside said hot box, and being configured to select a process path for the liquid reactants and the gases, thereby selecting whether or not the liquid reactants and the gases pass through said reactor, and being a six-way valve; and
    a separation system disposed outside said hotbox, and being configured to perform cold condensation under pressure and to separate the liquid products and the gas products by a level control system, said level control system configured to control the level in a separator recipient with an accumulated volume of 0.1-0.5 $cm^3$;
    said separation system having a minimum dead volume, and including a high resolution capacitive level sensor with a precision of ±0.1 $cm^3$ and a pressure control system;
    said separation system configured to permit continuous separation of the liquid products and the gas products and evacuation thereof from said separation system by different outlets;
    said level control system being configured to control a servo-positioned microregulation valve in a liquids output line, and said pressure control system being configured to control a servo-positioned microregulation valve inside said hot box in a gases output line and to control the reactor pressure; and
    said separation system being automated and computerized, having local control and remote control on-line, based on digital communications with a distributed control structure, a safety system being integrated into a microprocessor independent of said separation system.

2. An automatic reactor system according to claim 1, wherein said hot box is configured to maintain a temperature between 120-190° C. by a heater.

3. An automatic reactor system according to claim 1, wherein said catalyst forms a bed in said reactor, said bed including a thermocouple encapsulated in a sheath, without thermowell, which permits reaction temperature readings to be taken with response times of milliseconds.

4. An automatic reactor system according to claim 1, wherein said pressure control system includes a servo-positioned micrometer control valve.

5. An automatic reactor system according to claim 1, wherein said automatic reactor system includes a programmable automaton or microprocessor for management of different alarms.

6. An automatic reactor system according to claim 1, wherein said pump is a positive displacement pump.

* * * * *